United States Patent
Binnun (10) Patent No.: US 6,520,640 B1
(45) Date of Patent: Feb. 18, 2003

(54) ACQUIRING, ANALYZING AND IMAGING THREE-DIMENSIONAL RETINAL DATA

(75) Inventor: Emmanuel Binnun, Jerusalem (IL)

(73) Assignee: Talia Technology Ltd., Harey Yehuda (IL)

( * ) Notice: Subject to any disclaimer, the term of this patent is extended or adjusted under 35 U.S.C. 154(b) by 0 days.

(21) Appl. No.: 09/744,214
(22) PCT Filed: Jul. 21, 1999
(86) PCT No.: PCT/IL99/00400
§ 371 (c)(1), (2), (4) Date: Feb. 21, 2001
(87) PCT Pub. No.: WO00/04820
PCT Pub. Date: Feb. 3, 2000

(30) Foreign Application Priority Data

Jul. 23, 1998 (IL) .................................................. 125483

(51) Int. Cl.⁷ ................................................ A61B 3/14
(52) U.S. Cl. ..................................................... 351/206
(58) Field of Search ................................ 351/205, 206, 351/211, 214, 216, 221, 245, 246

(56) References Cited

U.S. PATENT DOCUMENTS 5,742,374 A   4/1998  Nanjo et al.
6,267,477 B1 * 7/2001  Karpol et al. ................ 351/221

FOREIGN PATENT DOCUMENTS

EP   0 380 197 A   8/1990
EP   0 412 667 A   2/1991
WO   97 30627 A    8/1997

* cited by examiner

Primary Examiner—George Manuel
(74) Attorney, Agent, or Firm—Lowe Hauptman Gilman & Berner, LLP (57) ABSTRACT

An apparatus for acquiring, analyzing and imaging retinal reflected data, comprises a combination of at least one digital fundus camera (11, 12, 49, 50) and a Retinal Thickness Analyzer (RTA) (18). Using common optical, electrical and mechanical components, including an optical combiner unit (64, 80), allows for a peripheral illumination and centered image acquisition of the eye fundus by a funduscamera, together with a lateral slit-illumination for sensing the retinal thickness by an off-center slit-camera (42). Additionally to the optical combiner unit, said common components may include: (a) an objective lens (9, 31 71); (b) a reticulation element (57, 66) for providing a fixation target; (c) means (90) for simultaneously focusing light beams of the RTA (18) and of the fundus camera; (d) processor (3) and displaying means (2) for displaying images of the retina (32), tailored from plurality of images acquired by the RTA and combined according to images acquired by the fundus camera; (e) an energy source (4); (f) a control panel and package; (g) a mechanical support for positioning the patient's face.

5 Claims, 6 Drawing Sheets

ACQUIRING, ANALYZING AND IMAGING THREE-DIMENSIONAL RETINAL DATA

FIELD OF THE INVENTION

The present invention generally relates to an apparatus and method for acquiring, analyzing and imaging of three dimensional retinal data.

More specifically the present invention relates to a non invasive apparatus and method for measuring retinal thickness, surface topography and other features relating to the structure of the retina together with digital imaging of the retina, and correlating said structure with the retinal image.

BACKGROUND OF THE INVENTION

The main cause of blindness in the western world is diabetic retinopathy. One of the most important pathologies of diabetic retinopathy is macular edema. Over a lifetime, about 30% of the people with diabetes will develop macular edema.

Non-proliferative diabetic retinopathy with Clinically Significant Macular Edema (CSME) includes either (a) thickening of the retina at or within 500 microns of the center of the macula or (b) hard exudates at or within 500 microns of the center of the macula if associated with thickening of the adjacent retina (not residual hard exudates remaining after the disappearance of retinal thickening) or (c) a zone or zones of retinal thickening 1 disk area or larger, any part of which is within 1 disk diameter of the center of the macula. Patients with CSME should be considered for treatment.

Recently a Retinal Thickness Analyzer (RTA) apparatus has been developed (U.S. Pat. No. 4,883,061). The RTA apparatus allows for visual inspection and for quantitative measurements of the retinal thickness, the amount of nerve fiber layer on the retina, the topography of the retinal surface, particularly that of the optic nerve head, and other additional features of the retina.

U.S. Pat. No. 5,742,374 teaches a fundus camera for photographing the fundus of an eye. The apparatus is provided with a ring slit illumination for peripheral illumination of the fundus. European Patent Publication No. 412667 teaches a fundus examining device including an optical system for observing an anterior portion of the eye. The apparatus disclosed is U.S. Pat. No. 5,742,374 and European Patent Publication No. 412667 are disadvantageous since the apparatuses disclosed do not enable analysis of the retinal thickness.

WO9730627 discloses a three dimensional imaging scanning apparatus for determining the retinal thickness and structure of the eye using non-invasive analysis. Optical paths and cameras are included for imaging both the whole fundus and the retinal thickness. For purposes of measurement of a specific region of the retina, both fundus imaging and imaging of the retinal thickness are used. The fundus imaging is specifically employed to determine relative positional orientation on the retina when selecting and also when subsequently comparing specific regions of the retina. Although WO9730627 utilizes a fundus camera, relatively complicated optics required for a professional fundus camera are not used. The fundus illumination is not homogeneous since it is performed in one direction (through the upper or lower part of the pupil). Imaging acquisition is also limited since it is not symmetric relative to the fundus. Therefore, the fundus camera can be used only as an accessory for a retinal thickness analyzer apparatus. The apparatus according to WO9730627 is disadvantageous since it can not be used as a medical diagnostic fundus camera device.

Also recently, fundus cameras used (i.e. for imaging retinas) are being modified for digital operation which allows for computerized processing, displaying and storing retinal electronic images.

The treatment for macular edema is by laser photocoagulation. The decision if and in what exact location on the retina the treatment is required, is based on an assessment regarding the retinal thickening and the location of the thickened areas.

The assessment of retinal thickening according to one known method is by slit lamp biomicroscopy and/or stereo fundus photography. The performance of this method is often difficult, inaccurate, and of questionable reliability. The information gained by using fundus cameras to perform Fluorescein Angiography shows areas of leakage in the retina which are seemed to be, but not necessarily are, the areas of thickening which have to be treated.

It is therefore of utmost necessity for an apparatus which may correlate the visual information gained from the fundus images with the thickness information gained from the RTA.

The present invention relates to such an apparatus, which combines the properties of an RTA and a digital fundus camera, by integrating the optical systems of the two instruments into a single system, which allows for acquirement of retina image data simultaneously (or in close succession) with retina thickness data, allowing a complete correlation in the registration of the two sets of data.

SUMMARY OF THE INVENTION

The present invention relates to an apparatus for acquiring, analyzing and imaging retinal reflected data, comprising a combination of at least one digital fundus camera and a Retinal Thickness Analyzer, using common optical, electrical and mechanical components, wherein a common optical combiner unit is included in the components, allowing peripheral illumination and centered image acquisition of the eye fundus by a fundus-camera, together with a lateral slit-illumination for sensing the retinal thickness by an off-center slit-camera Additionally to the optical combiner unit, the common components include at least one common component from the following; (a) a common objective lens; (b) a common reticulation element for providing a fixation target; (c) means for simultaneously focusing light beams of the RTA and of the fundus camera, going to and returning from the retina; (d) common processing and displaying means for displaying images of the retina structure, tailored from plurality of images acquired by the RTA and combined together according to images acquired by the fundus camera; (e) a common energy source; (f) common control panel and housing; (g) a common mechanical support for positioning the patient's face.

According to one variation of the apparatus, the common optical combiner unit is a removable dichroic mirror allowing acquisition of a high resolution slit image simultaneously with an average resolution fundus image, and the removable dichroic mirror is shifted out of the optical path for acquisition of a high resolution fundus image.

According to other variation of the apparatus, the common optical combiner unit is comprised of; (a) a central mirror for reflecting peripheral illumination onto the pupil and having an aperture at its center for transmitting the light returning from the retina to the fundus camera; (b) a first small mirror having an optical path disposed laterally off the center of the central mirror, for reflecting slit light onto the retina; (c) a second small mirror having an optical path disposed laterally off the center of the central mirror, for reflecting slit light returning from the retina to the slit camera; the two small mirrors are placed on two opposite sides of the central mirror. Preferably, the two small mirrors are integral parts of the central mirror, however, according to various considerations, they may also be positioned as separate parts, in front of the central mirror, or in the back of the central mirror, wherein the central mirror has two apertures conforming respectively with the optical paths of the small mirrors.

According to a preferred embodiment, the apparatus of the present invention has a first fundus camera for eye-fundus live image, and a second fundus camera for eye-fundus high resolution still image. Preferably, it further comprises a flash illumination source for acquiring still images.

In addition, the preferred embodiment of the apparatus comprise means for projecting a fixation target onto the examined eye of a patient, wherein the projecting means use at least in part the same optical path as the fundus camera. The embodiment also has a common focusing means for the slit light camera, the fundus camera and the fixation target projecting means.

The apparatus also utilizes a common power supply, a computer and a controlling unit for operating the slit light camera, the fundus camera, and associate electro-optical elements.

Preferably, the data acquired by the RTA slit camera and the data acquired by the fundus camera are combined automatically by the computer of the apparatus using an appropriate algorithm.

Preferably, in order to provide an improved distinction between light reflections associated with different cameras, the apparatus uses light sources of different wavelengths, or different color-filters.

Definitions

In the context of the present invention and accompanying claims, the term "digital fundus camera" relates only to a digital fundus camera. The term "fundus camera" relates to a digital fundus camera or a non-digital fundus camera.

The eye fundus analyzer apparatus according to the present invention has two basic modes of operation:

Mode A: Fundus Camera mode:

In this mode the apparatus operates as a normal digital fundus camera as follows:

A continuous wave light source (in the visible or infra red spectrum) illuminates the retina. This illumination is a light beam projected onto the retina through the pupil of the examined eye and it is shaped so as to go through a predefined area of the pupil (which can be doughnut shaped). Shaping the beam is achieved by a shaped mirror located at a position optically conjugate to the pupil. Preferably, the mirror is doughnut shaped (i.e. having a hole at its center). The operator is aligning the apparatus such that the shaped illumination beam is outlined exactly at the pupil of the examined eye. Various color filters may be inserted in the beam to provide different contrasts for different features of the imaged retina.

An electronic TV (monochrome or color) camera, images the retina. The objective lens of this camera is the same lens through which the illumination beam is projected onto the retina. The illumination beam returning light (that goes from the retina to the camera) is restricted to a certain area of the pupil which is separate from the area through which the illumination beam is projected into the eye. This is achieved by routing the light to the camera through an aperture which is placed at a position conjugate to the pupil. (The aperture can be in the same shaped mirror which deflects and shapes the illumination beam). The camera is focused on the retina by movements of one or more lenses in the optical path (the movements may be achieved in any way known in the art). The electronic signal from the camera is directed to a TV or computer monitor (which may be formed as part of the camera or separately). The image acquired by the camera is continuously displayed on this monitor. The live image can also be recorded and stored by different electronic image acquisition methods as known in the art.

In addition, one or more still images can be acquired by the same camera. According to an aspect of the present invention, a pulse of light (which differs from the illumination beam in spectral content and/or intensity) is injected into the illumination beam during the acquisition of the still image, for obtaining improved contrast and resolution effects in the still image.

According to another aspect of the invention, a special still camera (preferably a high resolution camera) is added as a part of the apparatus. It is used to acquire a still image taking the advantage of using live images for aligning the apparatus. For the acquisition of the still image, a pulsed light source such as a flash lamp is used, additionally to the live image illumination beam.

Mode B: Retinal Thickness Analyzer (RTA) mode:

In this mode the apparatus operates as a Retinal Thickness Analyzer as follows:

A narrow slit of light (preferably a laser light) is projected onto the retina through a decentred area of the pupil of the examined eye.

The narrow slit light which illuminates the retina differs from the fundus camera illumination beam in one or more of the following:

(a) Its spectral content is different than that of the fundus camera illumination beam.

(b) One or more fixation target patterns which are seen by the examined eye are added by either subtraction or addition of light from/to the beam.

(c) The area on the pupil through which the fundus camera illumination beam passes is other than that through which the slit light passes.

The slit light scattered back from the retina is viewed by an electronic camera (hereinafter called "slit camera"). The scattered light is restricted to pass through an area de-centered on the pupil and opposite to the area through which the slit light enters the eye. This is achieved by an aperture located on the light path at a point conjugate to the pupil. This causes the slit camera to view the slit image on the retina at an angle relative to the angle of the incident slit light. This allows for a quantitative measurement of the retinal thickness cross-section topography for the specific retinal area selected, and for optical sectioning of the retina.

During one measurement, the slit light is scanned over a number of positions on the retina so that the resulting image represents a number of cross-sections of the retina covering a square area of, for example, 2×2 mm. It is possible, for example, that nine adjacent squares are scanned to provide coverage of an area of about 6×6 mm (20"×20") around the fovea, disk, or any other interesting zone. Immediately after the acquisition of the slit image, a still fundus image is acquired. The relative location of the slit image (or images)

on the still image is known, according to the known relative positions of the optical paths used. This allows for a correlation between the information gained from the analysis of the slit images and the image information of the retina.

Likewise, numerous of either contiguous or dispersed scanned areas of the retina, can be represented in correlation with an image of the retina to enable a clinical and scientific evaluation.

BRIEF DESCRIPTION OF THE DRAWINGS

The present invention will be further described in detail with references to FIGS. 1–6. These figures are solely intended to illustrate the preferred embodiments of the invention and are not intended to limit the scope of the invention in any manner.

DETAILED DESCRIPTION OF THE INVENTION

Figure 1:
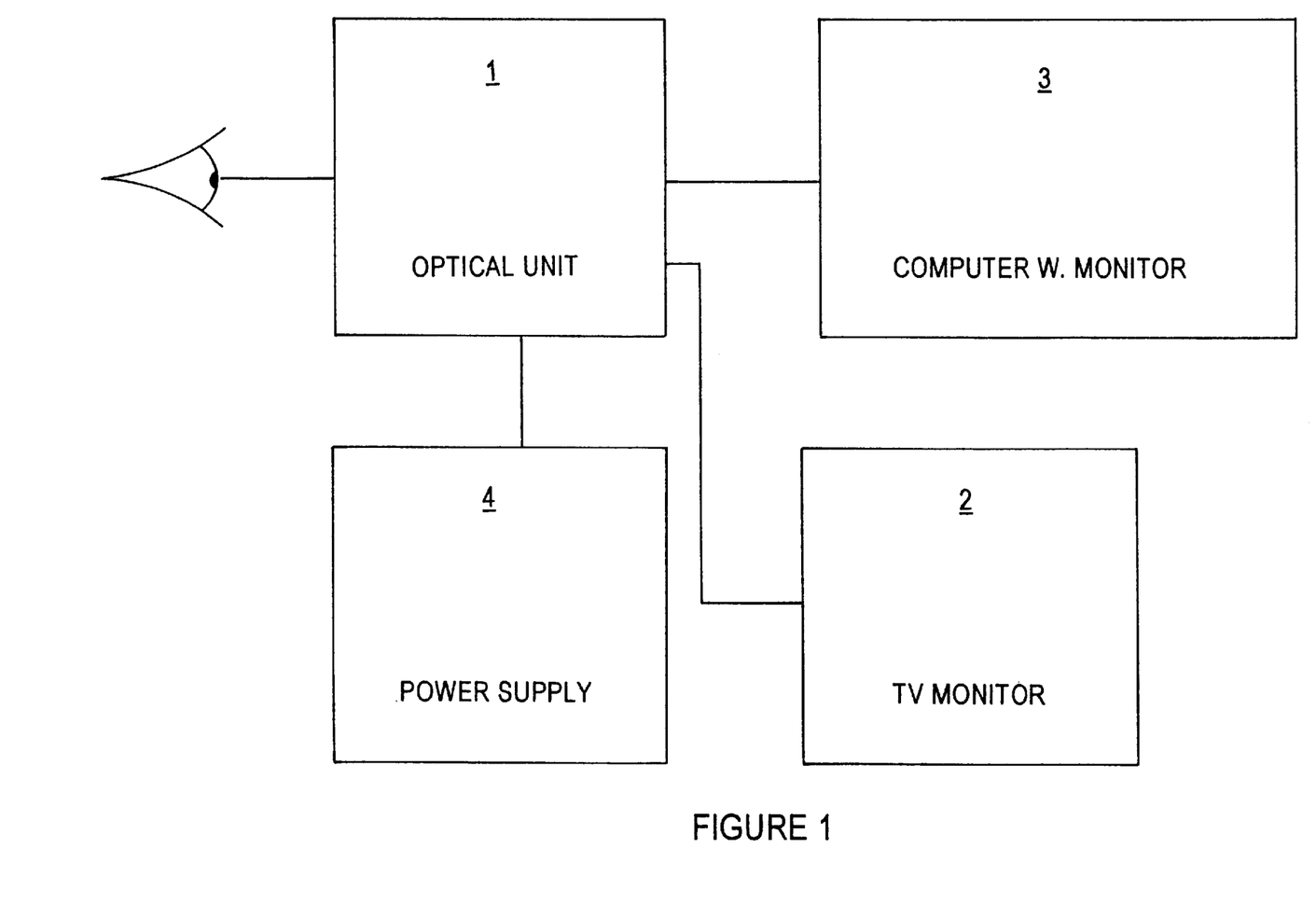
FIG. 1 illustrates a block diagram of the apparatus according to the present invention.

FIG. 1 shows a block diagram of the apparatus, comprising an optical unit (1), a TV monitor (2) a computer with monitor (3) and a power supply (4).

The optical unit illuminates the retina with several illumination units, and acquires images from the light returned from the retina by several cameras. Some of the images are displayed live on the TV monitor, and others are directed to the computer, displayed on its screen, stored, and analyzed. The power supply supplies power to various parts of the optical unit.

Figure 2:
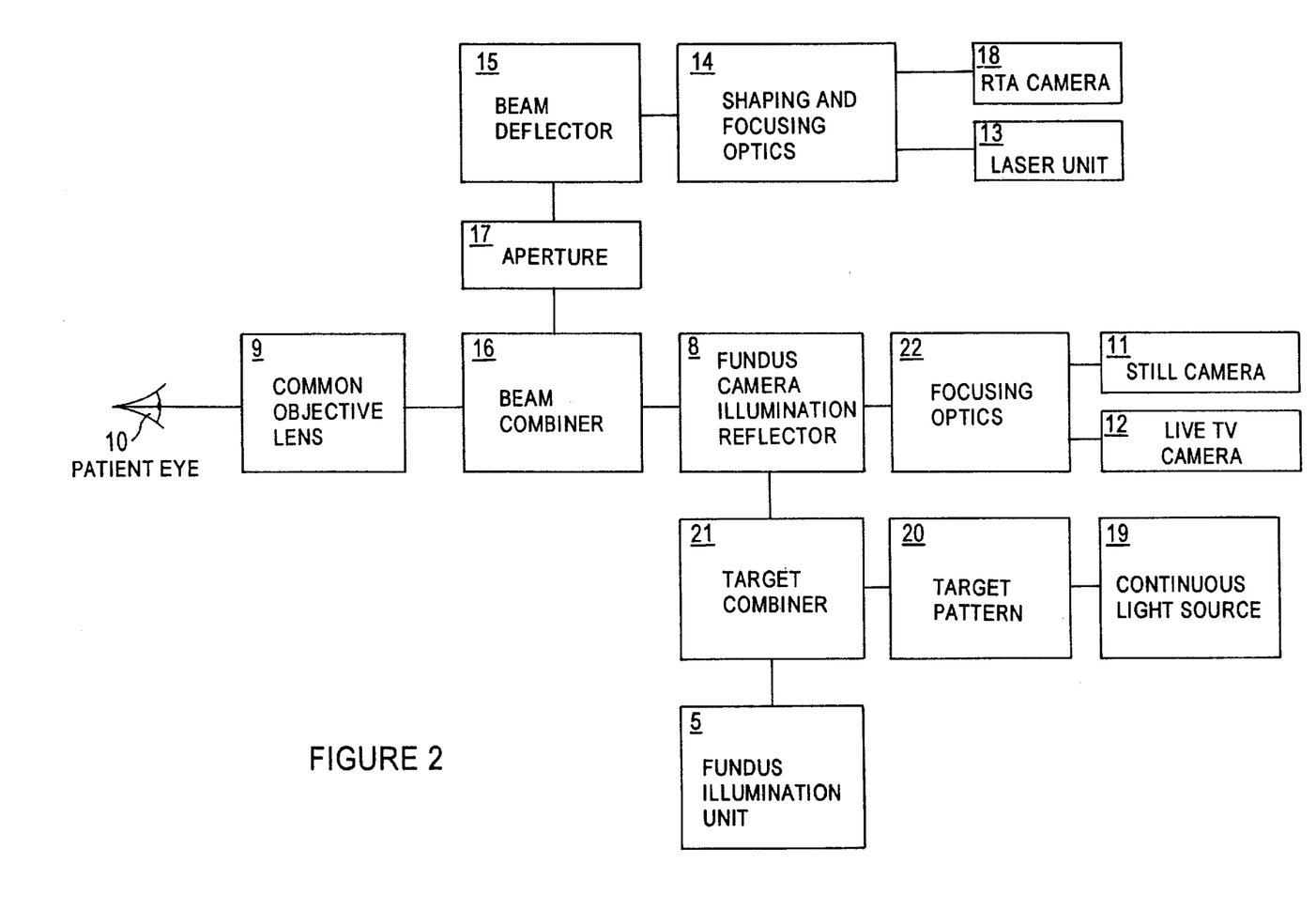
FIG. 2 illustrates a block diagram of the optical unit of the apparatus according to the present invention.

FIG. 2 illustrates a block diagram of the optical unit of the apparatus. In the optical unit of the apparatus according to the present invention, there is a fundus illumination unit (5) in which light originating from a light source passes through a condenser lens and through a filter unit. The light source contains a continuous light source such as a halogen lamp, and a pulsed light source such as a flash lamp. The light filtered by the filter unit, is reflected by a fundus camera illumination reflector (8) (for acquiring a high resolution fundus image, the target combiner (21) is eliminated when the optical path is operative), and through a common objective lens (9) into the eye (10) and onto its retina. Some portion of this incident light is reflected back through the same objective lens (9) and through an aperture in the center of the fundus camera illumination reflector (8) and through focusing optics (22), to one of two selectable electronic cameras (11, 12) which image the retina. One of the cameras is a live TV camera (12) which makes use of the continuous light source to provide a continuous live image of the retina. The other camera is a still camera (11) which acquires an instantaneous image during a momentary operation of a pulsed light source in the fundus illumination unit.

A second optical path in the optical unit begins with a laser beam generated by a laser unit (13) and projected through shaping and focusing optics (14) onto a beam deflector (15). The beam deflector is vibrated in time dependent back and forth angular movement, such that the laser beam is being deflected with respective angular variations, before it passes through the beam combiner (16) and through the common objective lens (9) into the eye (10) and its retina. Scattered light returning from the retinal tissues is passing back through the objective lens (9), the beam combiner (16), aperture (17), beam deflector (15), focusing optics (14), and at the end of the path is being detected by a TV camera (18) (CCD).

A third optical path in the optical unit begins with a continuous light source (19) such as a halogen lamp or a LED. The light is being projected through a target pattern (20) onto a target combiner (21), from which it passes through the fundus camera illumination reflector (8) and through the common objective lens (9) into the eye (10) and onto its retina, thus projecting the target pattern onto the patient eye.

In an alternative embodiment of the apparatus, an optical transparent element printed with the target pattern (20) is inserted into the beam of the continuous light source (5), generating the target image.

Figure 3:
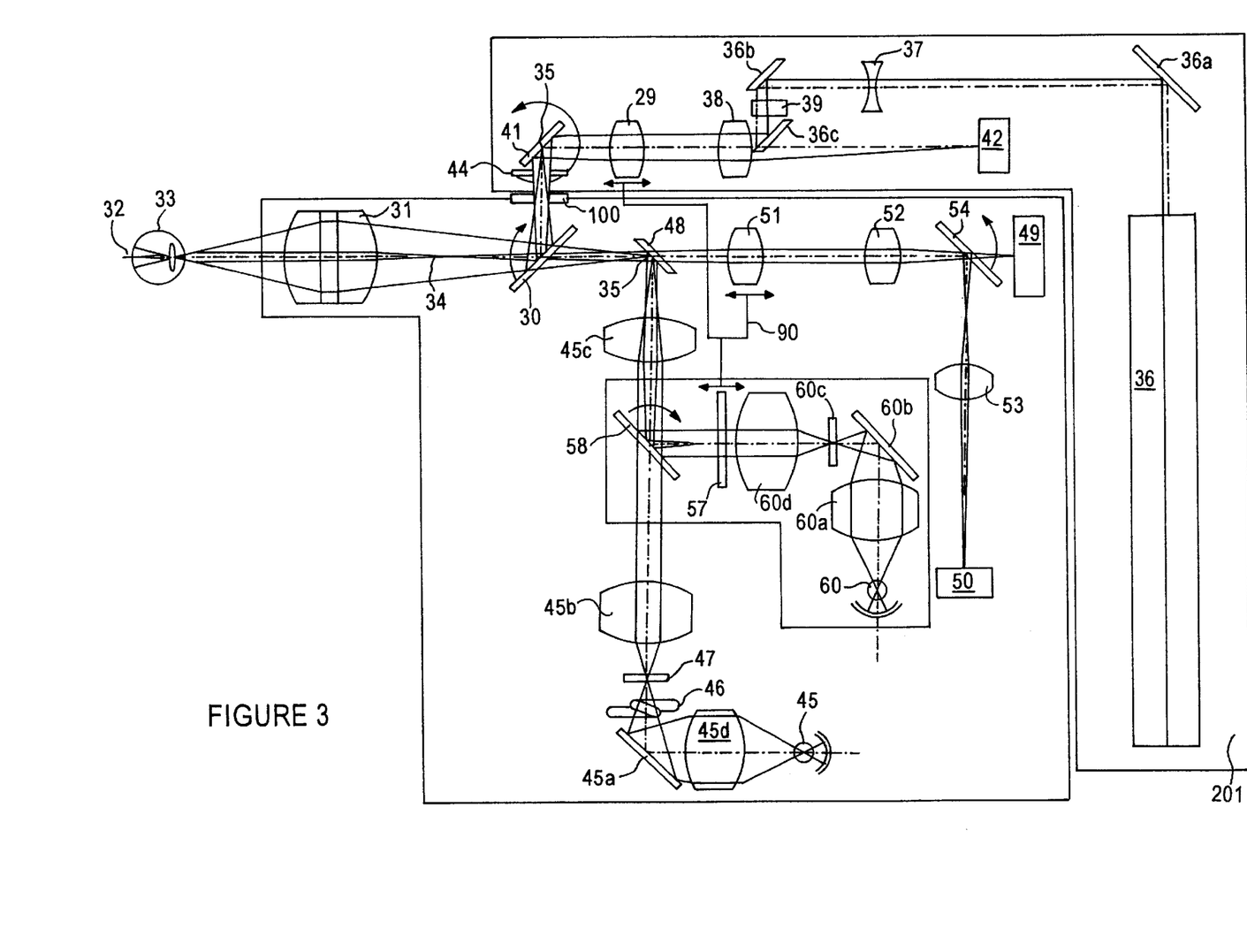
FIG. 3 is a schematic illustration of an embodiment of the major electro-optical components of the apparatus according to the present invention.

FIG. 3 shows how the optics and electronics of a digital fundus camera and an RTA are combined in the apparatus.

The objective lens (31) provides an image of the retina (32) of the examined eye (33) at an intermediate image position (34), near its focal plane, and another image of the pupil of the examined eye at points (35) conjugate to the pupil behind its focal plane. The objective lens is common to all (and in other variations of the apparatus to most) of the optical systems of the apparatus. This assures the exact spatial correlation between the retina thickness data and the fundus image, produced by the apparatus.

The objective lens (31) is common to the following optical systems:

(a) RTA Slit-light projection system which projects a vertical oriented slit of light on the retina. The system comprises a monochromatic light source (36), such as a laser unit. The light beam emitted from the light source (36) is directed through a reflective mirror (36a) for being expanded by a beam expander composed of a negative lens (37) and a positive lens (38). This positive lense (38) is used also in the slit-image acquisition system, which will be further explained in detail. The beam is slit shaped by means of a cylindrical lens (39) positioned in the optical path, between reflective mirrors (36b)(36c) which direct the beam along the required path. The beam is focused by a lens (29) on the intermediate image position (34). This lense (29) is controlled by common mechanical cams (90). A scanner (41) composed of a back and forth rotating mirror, is positioned at a point which is conjugate to the pupil of the examined eye (33). The slit light beam is offset horizontally from the optical axis at this point. This assures the correct horizontally de-centered positioning of the beam at the pupil, and its fixed location on the pupil during scanning. A window (100) allows the beam passing from the RTA projecting system to be reflected toward the objective lens (31) by means of a dichroic beam combiner (30). This combiner is designed to be switched out of the optical path when using the apparatus as a high resolution fundus camera. From the common objective lens (31), the slit light passes into the eye (33), and focuses on the retina (32).

(b) RTA Slit-light image acquisition system which acquires an image of the retina based on light returning therefrom when slit-light is projected on the retina by the slit light projection system. The system comprises a slit-light electronic camera (42) in which the image is acquired. The slit-light camera receives the image through the scanner (41), the focus lens (29) and the positive lens (38) which all are common with the slit-light projection system. The light reaching the slit-light camera returns from the retina through a specific area on the pupil which is spaced horizontally from the location through which the slit-light beam enters the pupil in its path into the eye. This is achieved and predetermined by light limitation means such as a buffering element having an aperture (44), placed at a location which is conjugate to the pupil.

(c) Fundus Camera Illumination system which illuminates the retina for image acquisition by the fundus cameras. The system comprises a continuous light source such as a halogen lamp (45) (which illuminates through lens (45d), reflective mirror (45a)) and a pulsed light source such as a flash lamp (46). Both light sources are filtered by means of color filters. The light sources illuminate through an aperture (47) which is located at a location conjugate to the pupil. This aperture is sized and shaped as required for obtaining on the pupil the desired shape of the fundus illumination beam.

The fundus illumination beam reaches the retina (32) after being passed through relay lenses (45b)(45c), deflected by a fundus camera illumination reflector (48) and passed through the common objective lens (31). The fundus camera illumination reflector (48) is located at a location conjugate to the image (35) of the pupil and is shaped so that only light in conformity with the desired shape of the beam at the pupil, is reflected towards the objective lens.

(d) Fundus camera image acquisition system which images the retina by the fundus cameras. The light scattered back from the retina (32) is focused by the objective lens (31) onto the intermediate image plane (34). The beam from the retina is limited, passing through an aperture in the fundus camera illumination reflector (48), so that only light returning from a desired area on the pupil, which differs from the area through which the light enters the eye, is passed through the aperture. The virtual image on the intermediate image plane is received either by the still camera (49) or by the live camera (50) through a focusing lens (51), imaging lenses (52) (53) and a flip mirror (54) which is controlled to switch the beam between the two cameras, according to the operator's request.

(e) RTA target system which projects a fixation target (or targets) onto the retina. A continuous light source (60) illuminates a target reticule (57), through condenser lens (60a), reflective mirror (60b), shaping aperture (60c) (located at a point conjugate to the pupil) and relay lens (60d). The beam from the light source (60) is combined with the fundus illumination beam, by means of a fixation target combiner made of a dichroic mirror (58). This combiner is switched out of the optical path when the apparatus is used in the fundus camera mode.

Focusing of the RTA slit-light projection and Slit-light image acquisition systems is achieved by movement of the common RTA focus lens (29). Focusing of the fundus camera images is achieved by movement of the fundus focus lens (51). Focusing of the target, is achieved by movement of the target reticule (57). It might not be necessary to focus the target because the depth of focus is large and can accommodate a large extent of the examined eyes. Correct focus movement of all elements is achieved simultaneously by means of the common mechanical cams (90).

The patient's eye and the optical systems of the apparatus are illustrated in the FIG. 3 as seen from above. In this embodiment, the illumination and optical systems of the fundus camera, and the RTA illumination and optical systems, are both in the same horizontal plane. However, according to different variations of the apparatus according to the present invention, they can also be arranged in planes which are perpendicular to each other, or they can both be arranged in a vertical plane, as long as the RTA slit-light illumination beam and the RTA camera return beam, enters and exits the patient eye horizontally (i.e. the entrance and exit locations of the beams at the eye are displaced horizontally).

Figure 4:
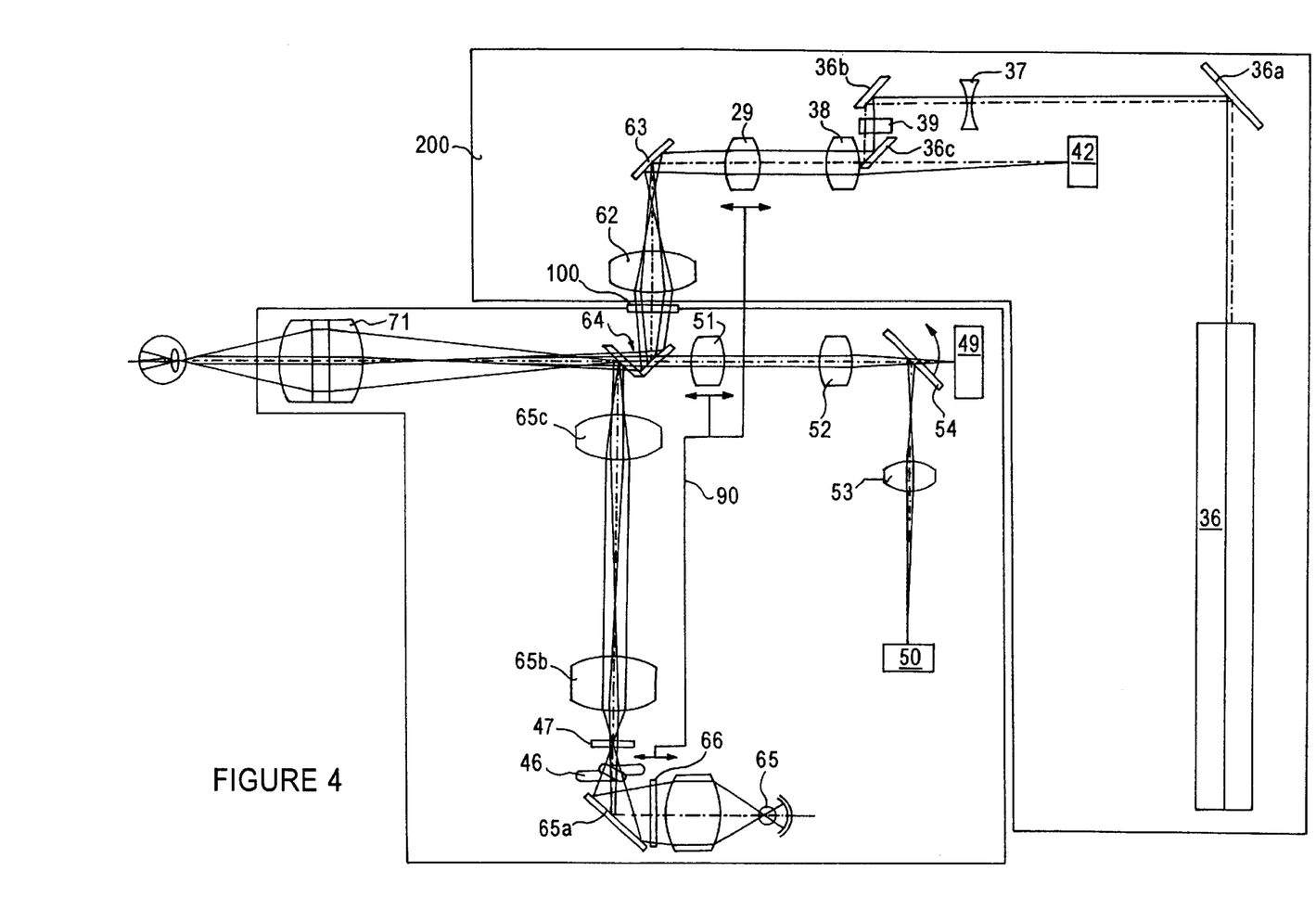
FIG. 4 is a schematic illustration of another embodiment of the major electro-optical components of the apparatus according to the present invention.

FIG. 4 illustrates another embodiment of the apparatus, having a different configuration of optical systems. In this figure, the optical systems are illustrated in a lateral view. In this embodiment, the RTA beams and the fundus-camera beams are combined in a reflective common combiner unit which is located at a location conjugate to the pupil. The RTA beam deflector (63) is also placed at an image of the pupil through introduction of an additional lens (62) which focuses the image of the pupil onto the beam deflector (63). The beam combiner (64) is made of two closely spaced mirrors, one deflects the fundus illumination beam which comes from the fundus illumination light source (65) toward the common objective lens (71) and into the eye, and the other deflects the RTA beam into the eye and from the eye into the slit-camera. In the mirror which deflects the fundus illumination, there are openings allowing the RTA slit projection beam and the RTA return beam to reach the other mirror. Both mirrors have a central opening to transmit the fundus camera beam toward the fundus cameras (49)(50). The combiner unit can also be made integrally as shown in FIG. 5.

In this embodiment, the illumination system for the RTA fixation-target uses the continuous light source of the fundus camera (65). A target reticulate slide (66) is inserted into the illumination beam at a location conjugate to the retina. This slide can have several target points so that different regions of the retina can be scanned by having the patient eye fixated at a different target point during each scan. It can also have one target point, movable under computer control. The slide is moved to place the target point at a desired position relatively to the optical axis so that when the patient's eye fixates at the point, the eye is positioned in the correct angular position relatively to the direction of the scanning beam, and thus the desired area on the retina is scanned.

Figure 5:
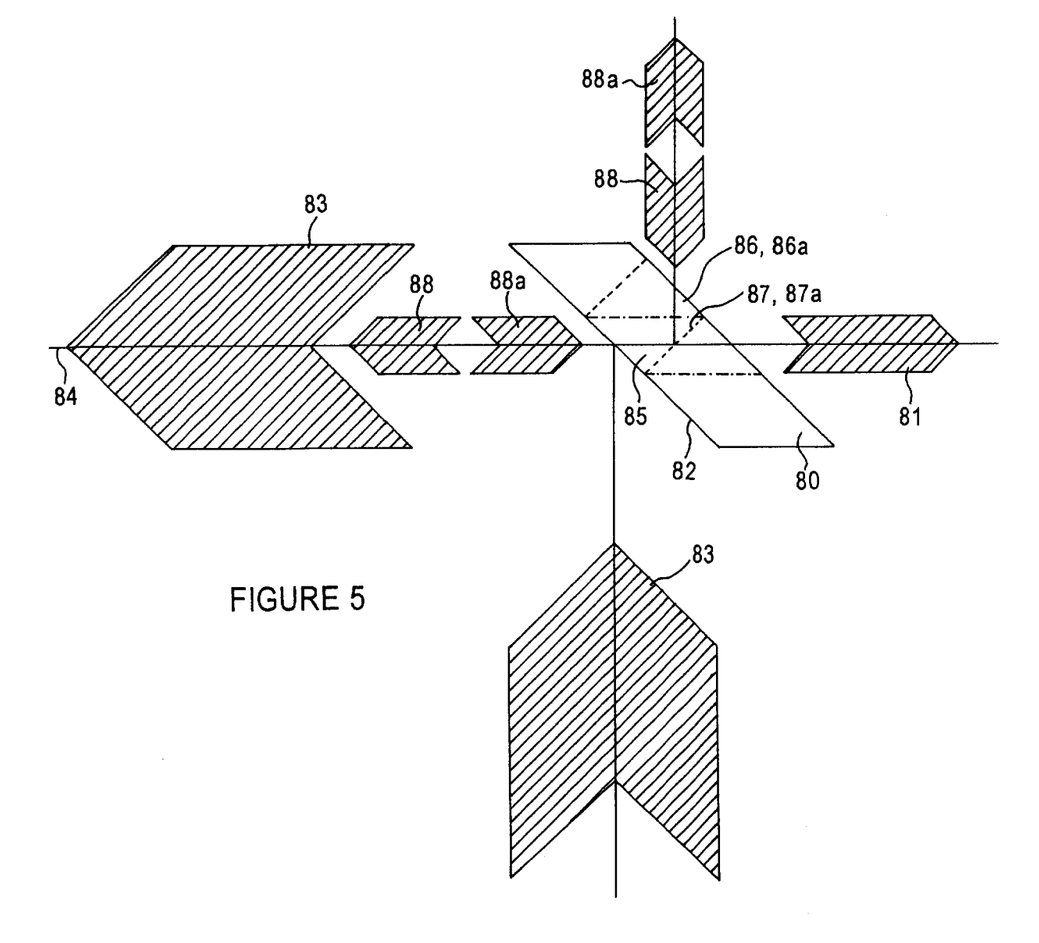
FIGS. 5 and 5A illustrate a beam combiner which combines the RTA and fundus camera optical beams, according to the embodiment illustrated in FIG. 4.

FIG. 5 shows a common beam combiner unit having three mirrors in one integral part, for combining all beams according to the optical layout shown in FIG. 4. The combiner is a plate of an elliptical shape in which openings for passage of light are cut. It also has several optically flat and reflective surfaces to reflect several beams of light. The combiner (80) is placed on the axis of the beam (81) which goes to the fundus camera. The reflective face (82) of the combiner is put at an angle of 45 degrees relatively to the optical axis of the beam going to the fundus camera, so as to reflect the fundus illumination beam (83) in the direction of the optical axis (84) which goes through the common objective lens. The combiner has a central opening (85) which allows passage of light from the retina to the fundus cameras. The size of the opening is selected so that its image on the pupil is of a desired size. The area of its face is optically flat and reflective. It reflects the fundus illumination beam towards the common objective lens. In this area there are two openings (86)(86a) which are laterally spaced from each other, and have optically flat reflective surfaces (87)(87a).

The RTA laser beam from the laser unit goes (88) through one of these openings and is reflected towards the common objective lens. The RTA beam (88a) returning from the retina, goes through the other opening and is reflected toward the RTA camera.

Figure 5A:
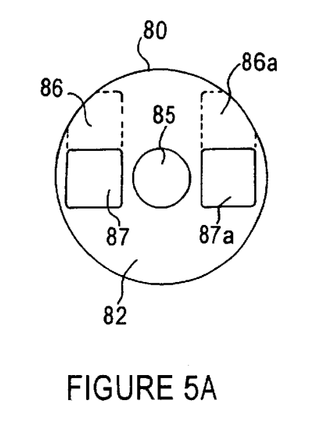

FIG. 5A illustrates the combiner (80) as seen from the objective lens direction. The central aperture (85) is for the beam (81) which goes to the fundus camera. Two openings (86)(86a) are laterally spaced from each other, and have optically flat reflective surfaces (87)(87a). The RTA laser beam from the laser unit goes through one of these openings and is reflected off the respective reflective surface ((87) or (87a)) towards the common objective lens. The RTA beam returning from the retina, goes through the other opening and is reflected off the respective reflective surface, toward the RTA camera.

Figure 6:
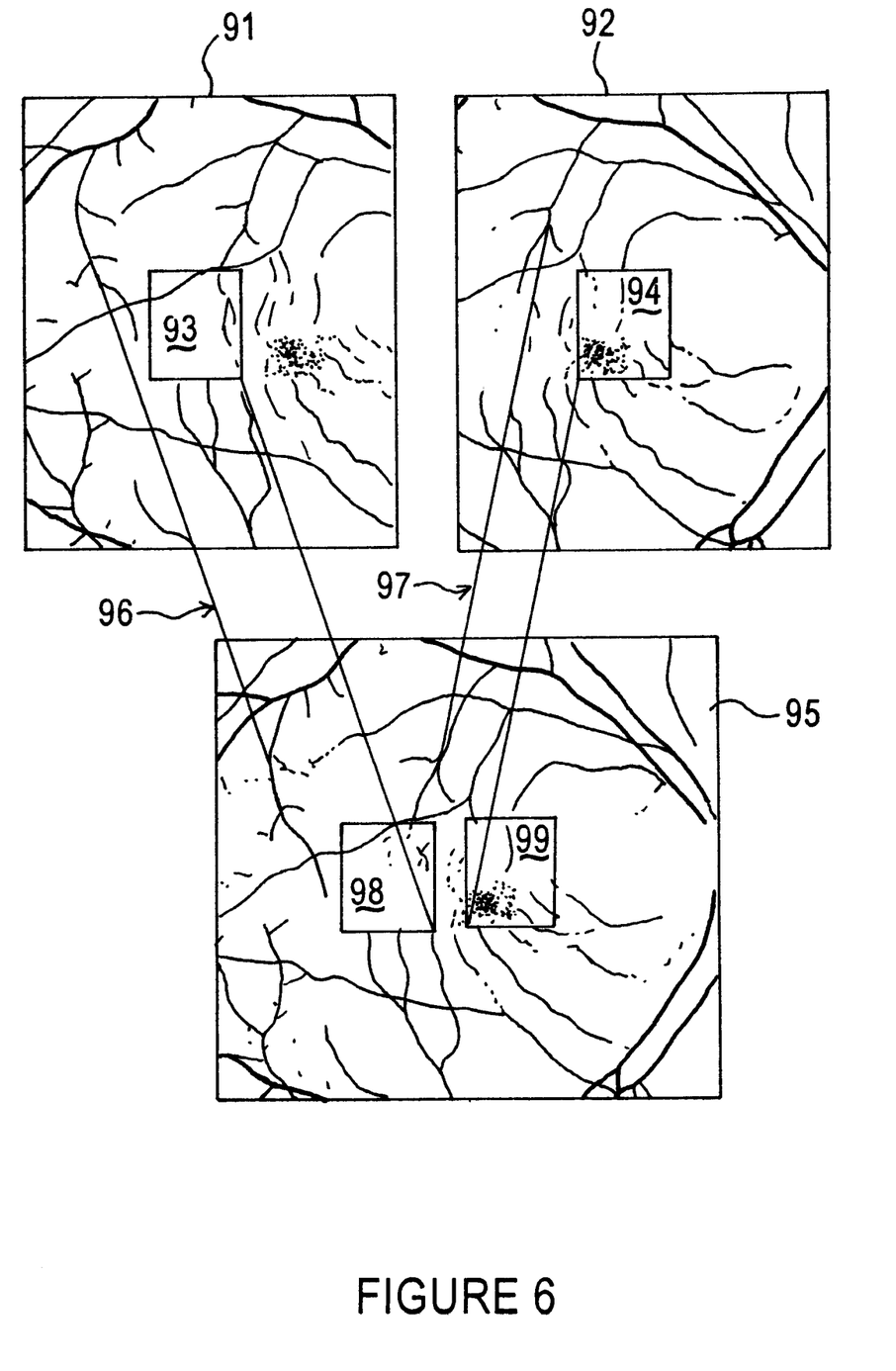
FIG. 6 schematically shows a method by which several scans of different areas of the retina are registered relative to each other.

FIG. 6 shows how scan images of different areas on the retina are registered relative to each other. Each RTA scan is accompanied by a stored fundus image. The figure shows two fundus images (91) and (92) corresponding to two scans of the same retina. The scanned area for which thickness data is calculated by the computer, is fixed relatively to the fundus image and is indicated by a rectangle in each fundus image such as rectangles (93) and (94). Another fundus image (95), is used to place several scan areas relatively to each other in a correct arrangement. This is done by computerized identification of items in the image (95), that are corresponding to items in the images (91)(92). The line (96) shows corresponding points in image (91) and (95), and the line (97) shows corresponding points in image (92) and (95). The translation corresponding to these lines is executed on the corresponding scan areas. Scan area (93) is translated by the translation defined by line (96) to the scan area (98) in image (95). In a similar manner scan area (94) is translated to scan area (99). In such a manner all scans done on the eye can be placed correctly relative to each other. The identification of corresponding points in the images can be done automatically by computer using feature extraction methods or by methods of cross correlation of the two images.

What is claimed is:

1. An apparatus for acquiring, analyzing and displaying images of a retina of an eye using light reflected therefrom, said apparatus comprising:

in combination, at least one digital fundus camera and a Retinal Thickness Analyzer (RTA), said digital fundus camera and RTA having common optical components; and a common driving mechanism coupled to simultaneously drive at least one optical component of each of said digital fundus camera and RTA;

wherein:

said common optical components comprise a common optical combiner unit positioned at a predetermined location for allowing peripheral illumination and centered image acquisition of the eye's fundus by said digital fundus-camera simultaneously with lateral slit illumination and retinal thickness acquisition of the eye by an off-center slit-camera of said RTA; and the common optical combiner unit is a removable dichroic mirror, the dichroic mirror being positionable at said predetermined location for allowing said digital fundus camera to acquire a lower resolution image of the fundus, and being movable out of said predetermined location for allowing said digital fundus camera to acquire a higher resolution image of the fundus.

2. An apparatus for acquiring, analyzing and displaying images of a retina of an eye using light reflected therefrom, said apparatus comprising:

in combination, at least one digital fundus camera and a Retinal Thickness Analyzer (RTA), said digital fundus camera and RTA having common optical components; and a common driving mechanism coupled to simultaneously drive at least one optical component of each of said digital fundus camera and RTA;

wherein said common optical components comprise a common optical combiner unit for allowing peripheral illumination and centered image acquisition of the eye's fundus by said digital fundus-camera simultaneously with lateral slit illumination and retinal thickness acquisition of the eye by an off-center slit-camera of said RTA, the common optical combiner unit comprising:

a central mirror for reflecting a fundus illumination beam onto the retina through the pupil of the eye, said central mirror having an aperture at a center thereof for transmitting said fundus illumination beam, which returns from the retina, to the digital fundus camera along a central optical path;

a first lateral mirror disposed laterally of the center of said central mirror for reflecting a slit illumination beam onto the retina along a first optical path; and a second lateral mirror disposed laterally of the center of said central mirror for reflecting said slit illumination beam, which returns from the retina, into the slit camera of said RTA along a second optical path, wherein said first and second lateral mirrors, as well as said first and second optical paths, are placed on opposite sides of said central mirror.

3. The apparatus according to claim 2, wherein the lateral mirrors of the combiner unit are integral parts of the central mirror.

4. The apparatus according to claim 2, wherein the lateral mirrors of the combiner unit are positioned upstream of the central mirror with respect to light returning from the retina to the combiner unit.

5. The apparatus according to claim 2, wherein the lateral mirrors of the combiner unit are positioned downstream of the central mirror with respect to light returning from the retina to the combiner unit, and wherein the central mirror has two lateral apertures on the opposite sides thereof, said lateral apertures being disposed respectively in the first and second optical paths of the lateral mirrors.

* * * * *